United States Patent
Bourges

(10) Patent No.: US 9,833,489 B2
(45) Date of Patent: Dec. 5, 2017

(54) USE OF SAFFRON AND/OR SAFRANAL AND/OR CROCIN AND/OR PICROCROCIN AND/OR DERIVATIVES THEREOF AS A SATEITY AGENT FOR TREATMENT OF OBESITY

(76) Inventor: Cedric Bourges, Plerin (FR)

( * ) Notice: Subject to any disclaimer, the term of this patent is extended or adjusted under 35 U.S.C. 154(b) by 0 days.

(21) Appl. No.: 13/156,984

(22) Filed: Jun. 9, 2011

(65) Prior Publication Data

US 2011/0236481 A1 Sep. 29, 2011

Related U.S. Application Data

(62) Division of application No. 12/298,242, filed as application No. PCT/FR2007/051158 on Apr. 23, 2007, now abandoned.

(30) Foreign Application Priority Data

Apr. 25, 2006 (FR) ...................... 06 51443

(51) Int. Cl.

| | |
|---|---|
| *A61K 36/88* | (2006.01) |
| *A61K 31/11* | (2006.01) |
| *A61K 31/351* | (2006.01) |
| *A61K 31/7028* | (2006.01) |
| *A23L 27/10* | (2016.01) |
| *A23L 33/105* | (2016.01) |

(52) U.S. Cl.
CPC .............. *A61K 36/88* (2013.01); *A23L 27/11* (2016.08); *A23L 27/115* (2016.08); *A23L 33/105* (2016.08); *A61K 31/11* (2013.01); *A61K 31/351* (2013.01); *A61K 31/7028* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2002/0128324 A1* | 9/2002 | Sunvold et al. | .............. 514/725 |
| 2005/0208156 A1* | 9/2005 | Ploch et al. | .................. 424/728 |

FOREIGN PATENT DOCUMENTS

| | | |
|---|---|---|
| EP | 1 481 675 | 12/2004 |
| JP | 63-295895 | 1/1990 |
| JP | 07135936 A * | 5/1995 |
| JP | 09202730 A * | 8/1997 |
| JP | 11302149 A | 11/1999 |
| JP | 2003206225 | 7/2003 |
| JP | 2003206225 A * | 7/2003 |
| JP | 2005527540 A | 9/2005 |
| JP | 2013216060 A | 10/2013 |

OTHER PUBLICATIONS

Gazzaniga. The no salt loweest-sodium cookbook. Macmillan. Jul. 31, 2002. p. 137.*
Balch et al. Prescription for natural cures. John Wiley & Sons. 2004. pp. 602.*
Hadizadeh et al. Evaluation of ISO Method in Saffron Qualification. Retrieved from the Internet on: Sep. 30, 2013. Retrieved from: <URL: http://confbank.um.ac.ir/modules/conf_display/conferences/saffron/pdf/p53.pdf>.*
Escribano et al. Cancer Letters, vol. 100, Issues 1-2, Feb. 27, 1996, pp. 23-30.*
Al-Mofleh et al. Pakistan Journal of Biological Sciences, vol. 9, No. 6 (2006) 1009-1013.*
"Basu Impex". Retrieved from the Internet on: Mar. 7, 2014. Retrieved from: <URL: http://basuimpex.com/uses.php>.*
Hosseinzadeh et al. BMC Pharmacology 2002, 2. pp. 1-8.*
Noorbala et al. Journal of Ethnopharmacology 97 (2005) 281-284.*
Database WPI Week 200374, Derwent Publications Ltd., London, GB, AN, 2003-783251, XP002414278.
Gassenheimer. A Fresh Idea for Tuna, Knight Ridder Tribune Business News, Washington, Apr. 20, 2006, p. 1 (pp. 1-2 in ProQuest).
Schlosser, The Herb Society of America's Essential Guide to Growing and Cooking with Herbs, LSU Press, 2007, p. 65.
Noorbala et al., Hydro-alcholic extract of Crocus sativus L. versus flouxetine in the treatment of mild to moderated depression: a double-blind, randomized pilot trial, Journal of Ethnopharmacology, 97, 2005, pp. 281-284.
Gennaro Remington, The Science and Practice of Pharmacy, Nineteenth Edition, vol. III, p. 1642.
Akhondzadeh et al., "Comparison of Crocus sativus L. and imipramine in the treatment of mild to moderate depression: A pilot double-blind randomized trial", BMC Complementary and Alternative Medicine, 2004, vol. 4.
Translation of Japanese Office Action dated Nov. 25, 2014, from corresponding JP application.

* cited by examiner

*Primary Examiner* — Amy L Clark
(74) *Attorney, Agent, or Firm* — Kramer Amado, P.C.

(57) ABSTRACT

Use of saffron and its active ingredients, such as safranal and/or picrocrocin and/or crocin and/or derivatives thereof, for the production of an active satiation agent for the treatment of problems of overweight.

13 Claims, 2 Drawing Sheets

Figure 3:
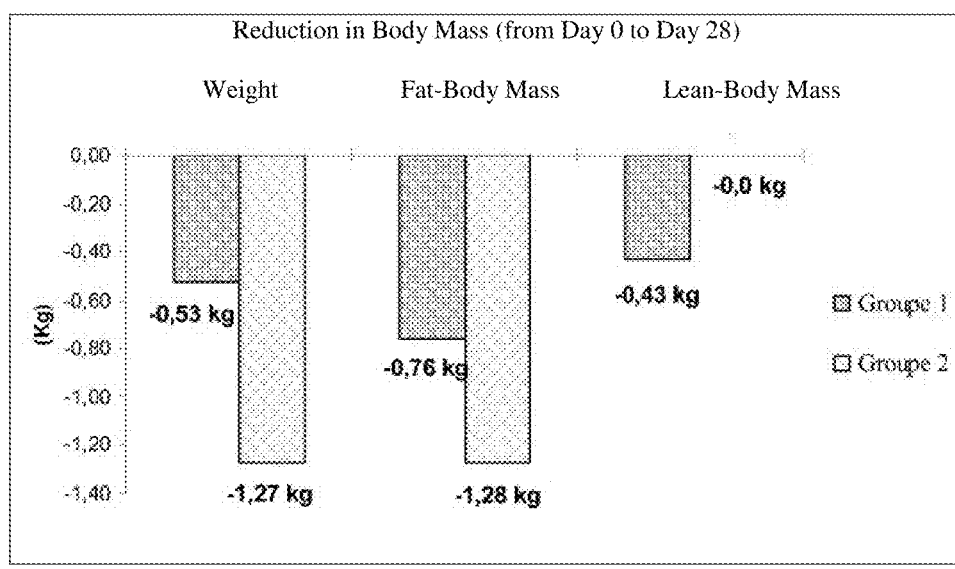

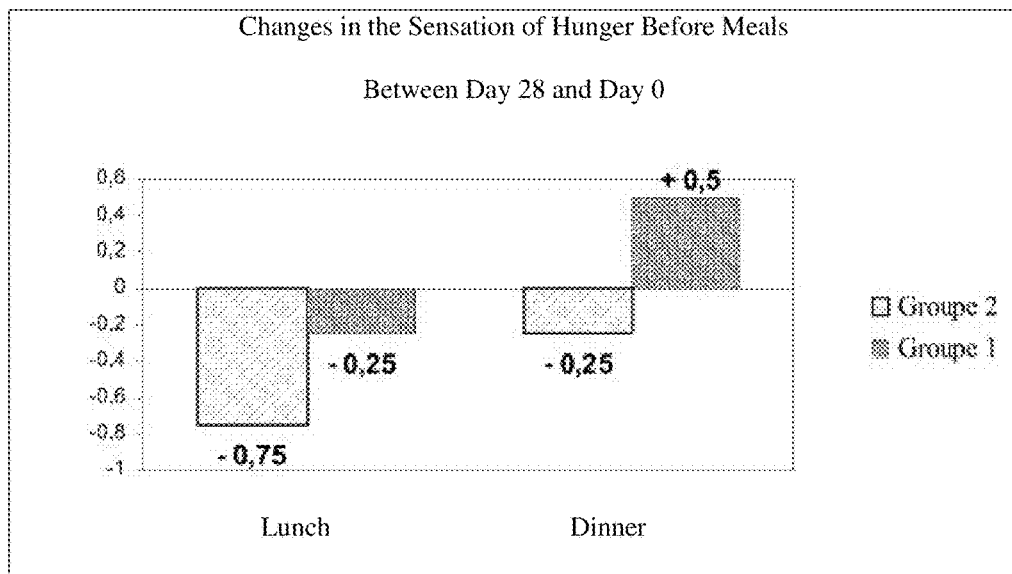
*Figure* 1
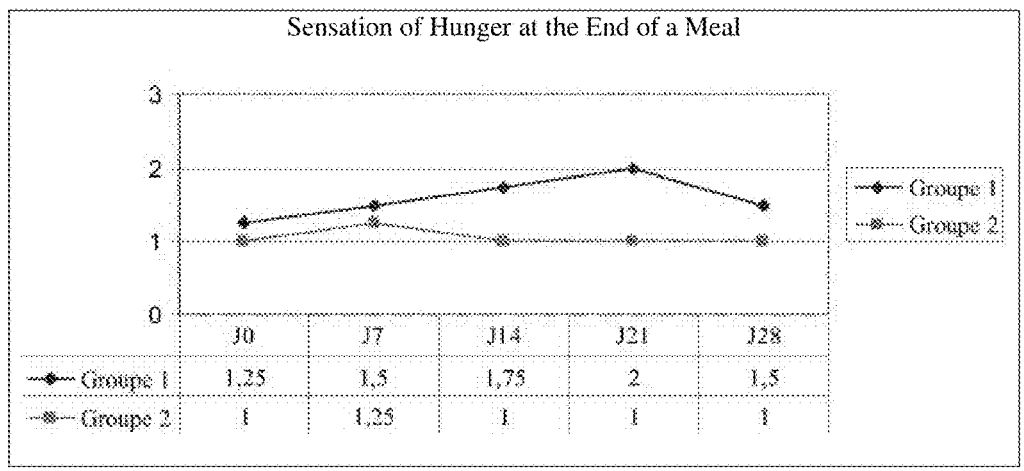
*Figure* 2
[Key:] Groupe = Group

USE OF SAFFRON AND/OR SAFRANAL AND/OR CROCIN AND/OR PICROCROCIN AND/OR DERIVATIVES THEREOF AS A SATEITY AGENT FOR TREATMENT OF OBESITY

This invention relates to the use of the active ingredients of saffron, in particular safranal, crocin, picrocrocin and derivatives thereof, for an application as a satiation agent.

The use of a satiation agent is useful in particular for the treatment of obesity, for reducing or at least controlling the intake of calories consumed daily so as to regulate body weight. Thus, the use of a satiation agent will allow the consumer, based on the alteration of the sensation of fullness, to control his physical appearance and/or to treat his health problems linked to overweight.

In addition to disagreeable mental circumstances (psychological problems) linked to the dictates of slimness and beauty in modern societies, a weight increase actually brings about health problems. The consequences of the problems of weight and obesity can range from an increase in premature death to non-fatal, but debilitating problems, having perverse effects on the quality of life. The primary health problems associated with obesity and overweight are: type 2 diabetes, cardiovascular diseases and high blood pressure, respiratory diseases (sleep apnea syndrome), certain cancers, and osteoarthritis. To this is added a reduction in the perception of the quality of life.

Various factors promote the increase of overweight.

The current diet is low in fruits and vegetables but in contrast very high in fat and heavy on sugar, meat and alcohol. In addition, water consumption is gradually being replaced by the consumption of sugary carbonated beverages. This dietary malnutrition brings about an increase in the number of calories consumed daily and thus a possible weight gain.

In addition, certain behaviors in the current lifestyle—such as inadequate physical activity, and individuals' frequent changes of habits—contribute more heavily to the risk of overweight.

In addition, taking certain common medications for treating ordinary diseases—such as cortisone as an anti-inflammatory, or citalopram, imipramine, paroxetine, cyamemazine, and bromazepam as anti-depressants—causes a significant weight gain.

However, it is not always obvious for an overweight person to follow a particular regimen, in particular because of the constraints that this requires and the difficulty of adapting it to the current lifestyle.

Numerous solutions have thus been proposed so as to help individuals control their weight.

For example, the use of medications suppressing the activity of enzymes in the digestive system. However, the use of such medications is required only for a medicinal purpose.

An invasive solution consists in the installation of a gastric ring so as to separate the stomach into two parts. Although this solution causes the sensation of hunger to disappear upon the ingestion of the first mouthfuls of a meal, the fact remains that this solution is used only in cases of extreme overweight. In addition, the risk of this surgical operation is significant.

Other products have been developed to induce weight loss, such as food substitution bars or beverages, most often based on dietary fibers, proteins, carboxymethyl cellulose and gums. However, the substitution proteins do not make it possible to satisfy the sensation of hunger until the next meal, consequently bringing about a risk that the consumer will nibble in order to satisfy this hunger.

Another approach in the treatment of overweight is the use of satiation agents so as to reduce the intake of energy, and therefore the weight.

The latter are most often contained in the food product that is to be consumed.

Some of these satiation agents are released directly into the stomach (WO 02/00042), and others act in different parts of the intestine so as to modify the response of the ileal brake (U.S. Pat. No. 6,267,988, U.S. Pat. No. 5,753,253, DE 2701361) or else some increase secretion of α-MSH by inhibiting the reuptake of dopamine or serotonin.

The document WO 01/17541 discloses a composition that comprises proteins, a high level of calcium, long-chain fatty acids, and an inhibitor source of the protease that is extracted from the potato so as to induce satiation.

The document WO 01/17377 discloses polysaccharides that contain uronic acid and that are cross-linked to one another so as to form a sponge-type structure that dissolves poorly in water, in stomach fluids and in the intestine or can be poorly resorbed. This composition has the purpose of providing a satiation effect.

US 2006/0040003 describes a composition for improving the satiation before and after the meal by raising the level of serotonin. This composition comprises natural substances such as, i.a., niacin, vitamin B6, calcium, phosphorus, magnesium, chitosan, and ginseng.

However, the compositions as described in the prior art have various drawbacks: the sensation of fullness does not always last very long. The food preparations (soups, bars) that contain the products are generally not very appetizing for the consumer. In addition, these compositions are not always easy to produce; some actually are not stable during the production process and/or storage, altering the taste, the odor and the texture of the final product. In addition, as appropriate, they optionally can have detrimental interactions with other active substances such as vitamins or minerals. Furthermore, products that contain synthetic chemical compounds, such as polymers, tend to discourage the consumer from purchasing them. This is why natural compounds are preferred.

Saffron is known in the prior art only as a stimulator of the gastric function, bitterness regulator, in particular after the intake of peppers (JP 2005 143308), or else it is used so as to improve the aroma in perfume compositions (EP 0162465).

The invention has as its object to propose a new use of saffron and its active ingredients that have numerous qualities and that make it possible to avoid all or part of the above-mentioned drawbacks. In particular, the invention has as its object to bring about a sensation of fullness in the overweight person, and even to treat the weight problems effectively without harmful secondary effects on the body, and without the consumer needing to modify his lifestyle or his dietary regimen.

For this purpose, the invention relates to the use of saffron and/or its active ingredients: saffron and/or picrocrocin and/or crocin and/or derivatives thereof in the production of an active satiation agent for the management and/or treatment of overweight.

The invention also relates to the use of saffron and/or its active ingredients: safranal and/or picrocrocin and/or crocin and/or derivatives thereof in the production of an active satiation agent for the management and/or the treatment of dietary problems, compulsive nibbling cravings linked to stress and/or depression.

The invention also has as its object the use of saffron and/or its active ingredients: safranal and/or picrocrocin and/or crocin and/or derivatives thereof for the production of an active satiation agent for the treatment of obesity.

Another object of the invention relates to the use of saffron and/or its active ingredients: safranal and/or picrocrocin and/or crocin and/or derivatives thereof for the production of an active satiation agent to help the overweight individual to reduce or control his daily calorie intake and/or to control his body weight and/or his physical appearance.

The invention also has as its object the use of saffron and/or its active ingredients: safranal and/or picrocrocin and/or crocin and/or derivatives thereof, in which this or these active ingredient(s) are combined with at least one inert excipient or vehicle, nontoxic, pharmaceutically and/or dietarily acceptable, making it possible to administer it orally.

Another object of the invention is the use of saffron and/or its active ingredients: safranal and/or picrocrocin and/or crocin and/or derivatives thereof, in which this or these active ingredient(s) come(s) in the form of a solution or an aqueous suspension in a glass ampoule, in a beverage, in a dropper bottle, in a spray or in the dry state of coated or uncoated tablets, gel capsules, capsules, powders, effervescent tablets, granules, strips, or lozenges.

In general, the content of safranal and/or picrocrocin and/or crocin and/or derivatives thereof is selected for an administration of between 0.05 mg/day and 100 mg/day, preferably between 0.2 mg/day and 10 mg/day.

Preferably, the content of safranal and/or picrocrocin and/or crocin and/or derivatives thereof within the satiation agent is between 0.01 and 50%—preferably between 0.05 and 20%, and more particularly between 0.1 and 10%—by weight, relative to the total weight of the satiation agent when the latter is found in solid form or relative to the volume of the satiation agent when the latter is found in liquid form.

Advantageously, the active ingredients of saffron are extracted by hydrodistillation followed by liquid/liquid extraction by polar and apolar organic solvents or by a vacuum microwave hydrodistillation (VMHD) or else by an extraction with supercritical $CO_2$ or with ultrasound, or with ion exchange resins with co-solvents and solvents of polar and/or apolar elution, or else by the set of solid/liquid extraction followed by liquid/liquid extractions.

The invention will be better understood, and other objects, details, characteristics and advantages of the latter will emerge more clearly during the following detailed explanatory description of embodiments of the invention that are provided by way of purely illustrative and non-limiting examples, with reference to the accompanying figures, in which:

FIG. 1 shows the mean changes in the sensation of hunger before the meal of 16 subjects having either received a placebo treatment for 28 days (group 1), or a composition that comprises a saffron stigmata extract according to this invention (group 2) between the end (day 28) and the beginning (day 0) of the experiment;

FIG. 2 shows the mean changes of the sensation of hunger of group 1 and group 2 at the end of the meal during the experiment from day 0 to day 28;

FIG. 3 shows the reduction in body mass by weight, by fat-body mass and by lean-body mass of group 1 and group 2 from day 0 to day 28.

As indicated above, it was found, surprisingly enough, that the active ingredients of saffron, such as safranal (2,6,6-trimethyl-1,3-cyclohexadiene-1-carboxaldehyde) of the following formula:

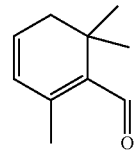

picrocrocin (4-(beta-D-glucopyranosyloxy)-2,6,6-trimethyl-1-cyclohexane-1-carboxaldehyde) and crocin (bis(6-O-beta-D-glucopyranosyl-beta-D-glycopyranosyl)8,8'diapo-psi, psi-carotenedioate) have proven effective in the treatment of weight problems of overweight individuals.

According to the World Health Organization, a person is overweight when his body mass index (BMI), which is equal to the weight in kg/(size in meters),$^2$ is between 25.0 and 29.9. If this index is above 30.0, the person is considered to be obese. This index thus makes it possible to estimate the nutritional state of a person and to know whether this person has excess fat in the body.

The active ingredients of saffron are extracted from a plant, the *Safran Crocus sativus* L., and more particularly stigmata of this plant. It is also possible to extract these active ingredients from other plants, such as *Yucca periculosa, Ditaxis heterantha, Cuminum cyminum, Gardenia jasminoides* or *Camelia Sinensis*.

The process that is used is known to one skilled in the art. It involves a first hydrodistillation stage, followed next by a second liquid/liquid extraction stage.

The hydrodistillation is used to extract the essential oil from the water-immiscible plant. The essence is entrained by the vapor in the form of a heteroazeotrope. The boiling point of the mixture is less than 100°. A mixture of organic substances and water is thus recovered. It is also possible to use pulsed vacuum microwave hydrodistillation (VMHD).

The liquid/liquid extraction is carried out by close contact of the solvent with the solution in equipment that is designed to mix the two phases (ampoules, columns, mixers). The separation of the phases is achieved by gravimetric decanting or centrifuging. The solvents that are used for the extraction are water and ethanol or else ethyl acetate, hexane, petroleum ether, acetone, or methanol.

The extraction of safranal, as well as other natural active ingredients of saffron, can also be done using supercritical $CO_2$, ideally at 100° C. and 20 MPa.

A syrupy liquid product, deep garnet red in color with iridescent reflections, is obtained at ambient temperature. It may also come in the form of powder after the water evaporates after, for example, oven-drying or atomization.

The thus extracted active ingredients: picrocrocin, safranal, and crocin also meet the ISO 3632 standards.

The satiation agent comprises a content of safranal and/or picrocrocin and/or crocin and/or derivatives thereof between 0.01 and 50%—but preferably a content of between 0.1 and 10%, and more particularly from 1 to 5%—by weight, relative to the total weight of the satiation agent when the latter is in solid or liquid form.

Other pharmaceutically and/or dietarily acceptable agents can be added to the satiation agent, such as bulking agents, fluidizing agents, natural extracts, vitamins, minerals, oligo elements, amino acids, fatty acids, anti-agglomerates, natural oils, aromas, dyes, acidifying agents, thickeners, preservatives and sweeteners.

The feedstocks are advantageously microcrystalline cellulose, potato maltodextrin, and magnesium lactate.

The thickener that is preferably used is potato starch, hydroxypropylmethyl cellulose, citrus pectin, guar gum, carob, agar-agar, konjac, hydrogenated oils, or beeswax.

The fluidizing agents can be magnesium silicate, magnesium stearate, and colloidal silica.

The anti-agglomerates are those usually used in the food industry, such as magnesium stearate and colloidal silica.

The vitamins are selected from among, i.a., vitamins C, E, $B_6$, $B_1$, $B_2$ and $B_3$.

The natural extracts in addition to the saffron stigmata extract can be extracts from green tea, cinnamon, guarana, Yerba Mate, fennel, queen of the meadow, corn, sage, bee balm, and caffeine.

As acidifying agent, citric acid can be used in the composition of the satiation agent.

The stabilizers used in the production of the satiation agent are those usually used in the agricultural industry, such as sorbitol.

The aromas that can be used are varied, such as the aroma of coffee, lemon, apple, chocolate, vanilla, and strawberry.

The sweeteners that are used are, i.a., xylitol, aspartame, glucose syrup, fructo-oligosaccharide syrup, maltitol in powder or in syrup form, acesulfame potassium, fructo-oligosaccharide, and sodium cyclamate.

Fatty acids can also be added to the satiation agent, such as omega 3, omega 6, Galacto, lipids, but also minerals: chromium, boron, magnesium, calcium, iron, molybdenum and amino acids, such as tryptophan, leucine, arginine and glycine.

Preservatives are useful so that the satiation agent is preserved over time. The preservatives that are used can be, for example, potassium sorbate, parabenes, sodium benzoate, or ascorbyl palmitate (anti-oxidant).

All of these compounds in no way limit pharmaceutically and dietarily acceptable agents that can be added to the composition of the satiation agent for the treatment of overweight.

The satiation agent that comprises, i.a., the active ingredients of saffron has the advantage of being easily usable and not restrictive. In addition, as the results below indicate, the content of active ingredients of saffron and more particularly safranal does not need to be very high to achieve the desired effect, i.e., an effect of satiation and therefore a very quick loss of weight of fat-body mass and in the circumference of the waist and hips. In contrast to satiation agents of the prior art, the saffron stigmata extract picked up in an ampoule or in a tablet does not have an odor, texture or taste that is disagreeable to the user. In addition, it is enough to take one or two daily doses, most often at breakfast and/or lunch so as to control or reduce the intake of calories during the day. Furthermore, as indicated above, the saffron stigmata extract can be combined with other active ingredients, such as vitamins, without this interacting with the effectiveness of the active ingredient. Finally, the satiation agent that is thus obtained is stable during its production and its storage.

The use of the saffron extract to help the overweight individual reduce or control his daily calorie intake and/or to control his body weight and/or his physical appearance can be done in different ways. Actually, this active ingredient can be very simply added to any commonly consumed food (beverages, prepared meals, . . . ) or else be in the form of a dietary addition, dietary products, a medical device, or medications. In this latter case, the concentration of saffron stigmata extract within the medication will be increased so that the satiation effect is felt more strongly. For example, a dose of saffron stigmata extract ranging from 60 to 150 mg per medication will be suitable in particular for persons suffering from the disease of obesity.

The following formulations (Tables 1 to 8) are provided by way of purely illustrative examples.

1) Size 12 Film-Coated Oval Tablet

TABLE 1

| Materials | Dose in mg |
|---|---|
| UNCOATED TABLET: | |
| Bulking agent: microcrystalline cellulose | 150.00 |
| Magnesium lactate | 254.00 |
| Saffron stigmata extract >2% safranal | 30.00 |
| Vitamin B6 | 2.00 |
| Bee balm extract | 10.00 |
| Fluidizing agent: magnesium silicate | 6.00 |
| Potato starch | 6.00 |
| Magnesium stearate | 5.00 |
| Colloidal silica | 2.00 |
| TOTAL UNCOATED | 465.00 |
| FILM-COATING | 18.60 |
| Sepifilm LP014 | 11.16 |
| Sepisperse dry 5221 | 7.44 |
| TOTAL FILM-COATED | 502.20 |

2) Size 1 Gel Capsule, Coating of Vegetable Origin

TABLE 2

| Ingredients | Dose (mg) |
|---|---|
| Bulking agent: potato maltodextrin | 80.00 |
| HPMC gel capsule | 80.00 |
| EGCG-rich green tea extract | 60.00 |
| Cinnamon bark extract | 50.00 |
| Saffron stigmata extract >2% safranal | 20.00 |
| Saffron stigmata powder | 20.00 |
| Vitamin B3 | 18.00 |
| Chromium chloride | 0.08 |
| Vitamin E in 50% powder form (calculation according to alpha-tocopherol LD 50%) | 20.00 |
| Bulking agent: MCC cellulose | 10.00 |
| Anti-agglomerate: magnesium stearate | 10.00 |
| Fluidizing agent: colloidal silica | 5.00 |
| TOTAL | 373.08 |

3) Soft Capsule

TABLE 3

| Ingredients | mg/Capsule |
|---|---|
| Wild fish oil with 30% omega 3 polyunsaturated fatty acids 18% EPA, 12% DHA | 577.00 |
| Saffron extract >2% safranal | 40.00 |
| Fish gelatin | 130.07 |
| Glycerol | 61.00 |
| Lemon aroma | 1.93 |
| TOTAL | 810.00 |

4) Effervescent Tablet

TABLE 4

| Ingredients | mg of Ingredient/Tablet |
| --- | --- |
| Acidifying agent: citric acid (E330) | 1070.00 |
| Sodium bicarbonate | 727.000 |
| Saffron stigmata extract >2% safranal | 60.000 |
| 20-30% catechin green tea leaf extract | 220.000 |
| Stabilizing agent: sorbitol | 146.000 |
| Vitamin C | 72.000 |
| 12% guarana caffeine extract | 70.000 |
| Green lemon powder aroma | 70.000 |
| 8% yerba-mate caffeine extract | 42.500 |
| Sweetener: aspartame | 30.000 |
| Yellow dye: tartrazine (E102) | 0.210 |
| Chromium chloride (19% chromium) | 0.025 |
| TOTAL | 2507.735 |

5) 10 ml Glass Ampoule

TABLE 5

| Ingredients | g/Ampoule |
| --- | --- |
| Aqueous extract concentrated by hot soaking of a mixture of plants: | 9.97 |
| Fennel - bulb - | 20% |
| Queen of the meadow - flowered head | 20% |
| Corn - stigmata - | 20% |
| Green tea - leaf - | 20% |
| Guarana - nut - | 20% |
| Saffron stigmata extract >2% safranal | 0.03 |
| TOTAL | 10.00 |

6) Beverage

TABLE 6

| Ingredients | mg/50 ml |
| --- | --- |
| Water | Sufficient quantity for 50 ml |
| Liquid saffron stigmata extract >2% safranal | 50.00 |
| Coffee aroma | 146.40 |
| Citric acid | 111.44 |
| Natural caffeine of coffee | 96.00 |
| Green tea leaf extract | 51.00 |
| Potassium sorbate | 50.00 |
| Sodium benzoate | 50.00 |
| Acesulfame potassium | 3.76 |
| Sodium cyclamate | 3.76 |
| TOTAL for 50 ml | 50,000.00 |

7) Squared

TABLE 7

| Ingredients | g/Squared |
| --- | --- |
| Citrus pectin | 3.600 |
| Guar gum | 2.258 |
| Glucose syrup | 1.660 |
| Fructo-oligosaccharide | 0.640 |
| Maltitol syrup | 0.670 |
| Maltitol powder | 0.500 |
| Apple aroma | 0.200 |
| Powdered glycerol | 0.190 |
| TCM oil | 0.136 |
| Water | 0.100 |
| Saffron stigmata liquid extract >2% safranal | 0.02 |

TABLE 7-continued

| Ingredients | g/Squared |
| --- | --- |
| Citric acid | 0.011 |
| Soybean tocopherol (67-75%) | 0.003 |
| Ascorbyl palmitate | 0.001 |
| TOTAL/SQUARED | 10.000 |

8) Granule

TABLE 8

| Ingredients | g/per 100 g of Granules |
| --- | --- |
| Citrus pectin | 75.00 |
| Microcrystalline cellulose | 20.00 |
| Sorbitol | 4.97 |
| Saffron stigmata extract >2% safranal | 0.03 |
| TOTAL | 100.00 |

Experimental tests have been performed so as to demonstrate the various actions of the satiation agent according to this invention:

Dosage 1

The effectiveness of the satiation agent that contains safranal has been tested on a panel of four persons for a duration of 20 days. These four persons have in no way modified their dietary habits nor their lifestyle during the period of the experiment. They have ingested 30 mg of saffron extract in a single dose daily at breakfast.

They felt a very slight reduction of hunger at lunch and dinner. A loss of weight on average of 1 kg, as well as a reduction in the circumference of the waist by 1.2 cm and in the circumference of the hip by 0.5 cm for each person have been noted.

This experimental test shows the surprising and unexpected effect of safranal on the regulation of hunger, whereas the saffron is usually used as an aroma or as a softener of the bitterness of certain foods.

Dosage 2: Double-Blind Vs. Placebo Clinical Test

A second clinical study was conducted so as to demonstrate the satiating effect of the active ingredients of saffron in 16 female subjects suffering from compulsive nibbling. The study was conducted over a period of four weeks. The healthy women were slightly overweight, i.e., a BMI of between 22 and 30.

A randomization method was implemented so as to divide these 16 subjects into two groups of 8. A first group (group 1) took 2 placebo gel capsules each morning and mid-day, while the second group (group 2) took two gel capsules/day, also in the morning and at mid-day, of a composition containing a saffron stigmata extract, whereby the two groups each received dietary counseling.

The composition that contains a saffron extract that was tested on group 2 comprised, i.a., gel capsules of 267 mg+/−10%; 90 mg of saffron stigmata extract stabilized on a microcrystalline cellulose substrate, and colloidal silica; and fatty acids rich in safranal, crocin and picrococin; 100 mg of maltodextrin; and 2 mg of magnesium stearate. More particularly, each gel capsule contained 0.9% picrocrocin (or 2.40 mg/gel capsule), 0.4% safranal (or 1.07 mg/gel capsule), and 0.3% crocin (or 0.80 mg/gel capsule).

Various indicators of effectiveness, such as measurements of weight, fat-body mass, hydric mass and BMI, have been measured, accompanied by a self-evaluation of the sensation of hunger, amounts consumed during, between and after meals. This self-evaluation of the sensation of hunger was measured by means of a subjective evaluation established by a digital visual method known to one skilled in the art.

First, as FIG. 1—which shows the demonstration of the sensation of hunger before meals between day 28 and day 0—illustrates, the subjects of group 2 felt a greater reduction of the sensation of hunger before lunch, continuing until dinner, while group 1 (placebo) felt an increase in the sensation of hunger.

At the end of the meal, as FIG. 2 illustrates, group 2 has not felt a sensation of hunger at the end of the meal (no variations), while group 1 (placebo) felt an increase from day 0 to day 28.

According to FIG. 3, which shows the reduction in body mass from day 0 to day 28, after 28 days of treatment of 2 gel capsules per day, one in the morning and one at mid-day, a loss of weight on average of −1.28 kg was noted in group 2 relative to a loss of weight on average of −0.50 kg within group 1; a loss of fat-body mass on average of −1.28 kg in group 2 relative to the placebo group 1 of −0.17 kg; and a loss of lean-body mass of 0 kg within group 2 relative to the placebo group that lost on average −0.33 kg.

Thus, 100% of the women receiving gel capsules comprising the active ingredients of saffron, i.e., a composition according to this invention, attested to having perceived a reduction in their sensation of hunger at the time of lunch and dinner and declared having reduced their food intake during the study. In contrast, none of the women taking the placebo noted a reduction in their food intake.

In addition, 25% of the women receiving the gel capsules according to this invention characterized their food intake as "much reduced" during the study.

Furthermore, the most significant loss of weight (−3.5 kg) was measured in the woman who believed her food intake to be "much reduced" during the study.

The reduction of the food intake in group 2 is thus connected to an increase in the sensation of fullness that, in contrast to the cognitive restriction, does not induce a sensation of frustration that increases the risk for regaining weight.

In comparison to the placebo group (group 1), the supplementation with gel capsules containing a saffron extract and consequently safranal, crocin, and picrocrocin, promoted the loss of weight, the loss of physical fat-body mass while keeping the lean-body mass and therefore the muscular mass stable.

The mean loss of weight is certainly modest, but it is probably clinically significant because of the absence of an associated low-calorie regimen, whereby the subjects have only received dietary counseling (for example, nibbling had been discouraged but not forbidden), and the short duration of the study relative to this problem.

Within the scope of a low-calorie regimen: reducing the sensation of restriction could improve compliance with the regimen and associated loss of weight, as well as to reduce the risk of rebound, often linked to a slackening following the regimen period.

In the long term (without an associated regimen), improving the ability of a subject to manage his dietary behavior can prove advantageous when he knows that avoiding an excess of 20 Kcal/day (or the equivalent of a piece of sugar) can prevent a weight gain of 1 kg of fat-body mass in 1 year (Ancellin, R., "Glucides et santé: état des lieux, évaluations et recommandations [Saccharides and Health: Assessments, Evaluations and Recommendations]," 2003).

The invention claimed is:

1. A method of treating an overweight or obese subject, comprising: orally administering to said subject a composition containing an effective amount of saffron stigmata solvent extract including a combination of picrocrocin, safranal and crocin, wherein said saffron stigmata solvent extract is obtained by:
  a.) isolating saffron stigmata; and
  b.) extracting the isolated saffron stigmata with a solvent, and wherein the effective amount of saffron stigmata solvent extract reduces fat-body mass while keeping lean-body mass and muscular mass stable.

2. The method according to claim 1, wherein, the composition further comprises at least one pharmaceutically and/or dietarily acceptable excipient or vehicle in the composition.

3. The method according to claim 1, wherein, the composition comprises a dose of the saffron stigmata solvent extract in an amount ranging from 60 mg to 150 mg.

4. The method according to claim 1, wherein, the composition is a solid form or a liquid form and the saffron stigmata extract is present in an amount of between 0.01 and 50% relative to the total weight of the solid form or relative to the volume of the liquid form.

5. The method according to claim 4, wherein the saffron stigmata extract is present in an amount of between 0.05 and 20% relative to the total weight of the solid form or relative to the volume of the liquid form.

6. The method according to claim 5, wherein the saffron stigmata extract is present in an amount of between 0.1 and 10% relative to the total weight of the solid form or relative to the volume of the liquid form.

7. The method according to claim 1, wherein the composition is in a form selected from the group consisting of a solution or an aqueous suspension in a glass ampoule, a spray, a beverage, a form suitable for a dropper bottle, one or more coated or uncoated tablets, one or more gel capsules, one or more capsules, powder, one or more effervescent tablets, granules, one or more strips, and one or more lozenges.

8. The method according to claim 1, wherein the saffron stigmata extract is extracted from saffron stigmata by hydrodistillation followed by liquid/liquid extraction.

9. The method according to claim 8, wherein the liquid/liquid extraction utilizes water and a solvent selected from the group consisting of ethanol, ethyl acetate, hexane, petroleum ether, acetone or methanol.

10. The method according to claim 9, wherein the liquid/liquid extraction utilizes water and ethanol.

11. The method according to claim 1, wherein the saffron stigmata extract includes a combination of picrocrocin, safranal and crocin.

12. The method according to claim 11, wherein said saffron stigmata is obtained from Safran *Crocus sativus* L.

13. A method of reducing or controlling caloric intake of calories consumed on a daily basis to regulate body weight in a subject in need thereof, comprising: orally administering to said subject a composition containing an effective amount of saffron stigmata solvent extract including a combination of picrocrocin, safranal and crocin, wherein said saffron stigmata solvent extract is obtained by:
  a.) isolating saffron stigmata; and
  b.) extracting the isolated saffron stigmata with a solvent, and wherein the effective amount of saffron stigmata solvent extract reduces hunger sensation, and wherein said subject is overweight or obese.

* * * * *